United States Patent [19]

Motamedi et al.

[11] Patent Number: 5,622,866
[45] Date of Patent: Apr. 22, 1997

[54] EXPRESSION CASSETTES USEFUL IN CONSTRUCTION OF INTEGRATIVE AND REPLICATIVE EXPRESSION VECTORS FOR STREPTOMYCES

[75] Inventors: Haideh Motamedi; Ali Shafiee, both of Westfield, N.J.

[73] Assignee: Merck & Co., Inc., Rahway, N.J.

[21] Appl. No.: 264,861

[22] Filed: Jun. 23, 1994

[51] Int. Cl.$^6$ .......................... C12N 15/63; C12N 15/00; C12N 1/20; C07H 21/04

[52] U.S. Cl. .................. 435/320.1; 435/69.1; 435/71.2; 435/71.3; 435/172.1; 435/172.3; 435/252.35; 536/23.2

[58] Field of Search .............................. 435/320.1, 172.3, 435/252.35, 69.1, 71.2, 71.3, 172.1; 536/23.2

[56] References Cited

U.S. PATENT DOCUMENTS

| | | | |
|---|---|---|---|
| 5,063,155 | 11/1991 | Cox et al. | 435/76 |
| 5,264,355 | 11/1993 | Shafiee et al. | 435/192 |
| 5,326,858 | 7/1994 | Lichenstein et al. | 536/23.2 |

OTHER PUBLICATIONS

Inokoshia et al., Gene 119:29–35 (1992).
Lydiate et al., Mol. Gen. Genet., 203:79–88 (1986).
Bibb et al., 5th Intl. Symp. on Genet. of Ind. Microog. 309–318 (1986).
Gold et al. Methods in Enzymology 185:89–93 (1990).
Vijgenboon et al., Microbiology 140:983–998 (1994).
Malpartida et al., Biochem. Biophys. Res. Comm. 117(1):6–12 (1983).
Pouwels, et al., in Cloning Vectors, Elsevier, (1985) pp. IIIA–i–6—IIIA–ii–1.
Omer et al., T. Bacteriol. 170(5):2174–2184 (1988).

Primary Examiner—George C. Elliott
Assistant Examiner—John S. Brusca
Attorney, Agent, or Firm—J. Eric Thies; David L. Rose

[57] ABSTRACT

The present invention is directed to expression cassettes useful in gene expression studies in both homologous and heterologous Streptomyces strains. More specifically the present invention is directed to the construction of two *Streptomyces lividans*-recombinant strains capable of producing 31-O-desmethylFK-506 O:methyltransferase, which methylates 31-O-desmethylFK-506 to FK-506. In addition, the present invention is directed to a process for the specific methylation of 31-desmethyl-FK506 to FK506.

20 Claims, 7 Drawing Sheets

EXPRESSION CASSETTES USEFUL IN CONSTRUCTION OF INTEGRATIVE AND REPLICATIVE EXPRESSION VECTORS FOR STREPTOMYCES

BACKGROUND OF THE INVENTION

1. Field of the Invention

The present invention relates to the construction of expression cassettes for use in gene expression studies in both homologous and heterologous Streptomyces strain background. Specifically this invention describes construction of two *Streptomyces lividans*-recombinant strains capable of producing 31-O-desmethylFK-506 O:methyltransferase, which methylates 31-O-desmethylFK-506 to FK-506.

2. Brief Description of Disclosures in the Art

The economic potential of DNA recombinant technology in producing unlimited amount of the pharmaceutically valuable peptides and proteins is vast. For example, the biologically active peptides and proteins such as insulin, erythropoietin, granulocyte-colony stimulating factor (G-CSF) and other important growth factors can now be produced in an unlimited quantities in bacteria, yeast and mammalian cell lines. Similarly, unlimited amounts of catalytic proteins (enzymes) may also be produced. This is significant because the use of enzymes as catalytic reagents in the synthesis of organic compounds are becoming increasingly practical and popular, not only because of economic factors, but also due to convenience in carrying out the chemical reactions, and environmental concerns where the use of toxic organic chemicals and solvents needs to be reduced or eliminated. In addition, enzymes are capable of catalyzing certain reactions that might otherwise be impossible or difficult to carry out by traditional organic reagents. To exploit DNA recombinant technology, however, it is essential that a large scale fermentation technology is available. Furthermore, it is equally critical that the bioconverting cultures and/or purified catalytic proteins capable of catalyzing particular organic reactions are accessible.

Regarding large scale fermentation, the technology is well developed for the microorganisms belonging to the genus Streptomyces; a large number of the secondary metabolites and extracellular enzymes are commercially produced by the fermentation of this microorganism. With regard to the availability of the bioconverting cultures and/or purified proteins, these cultures and proteins have to be discovered, isolated and/or made by using a genetic engineering approach. There is a long felt need in the art for different cultures which are capable of catalyzing a variety of organic reactions. The present invention meets this need by providing expression systems for the introduction of a single gene into the Streptomyces chromosome which enables the host organism to produce proteins with particular desirable catalytic properties. Furthermore, the present expression systems may be transferred as cassettes onto low as well as high copy Streptomyces replicating plasmids for the production of large quantities of a desired compound.

BRIEF DESCRIPTION OF THE FIGURES

FIG. 2: Schematic representation of the components used in the construction of the integralive expression vector, wherein:

"Perm E*" is a promoter fragrant derived from erythromycin resistance gene of *Saccharopolyspora erythrea* (Bibb, M. J., et al., *Mol. Gen. Genetic* 199:26–36 (1985), Bibb, M. J., et al., *Fifth Int'l Symp. on the Genetics of Industrial Microorganisms,* 309–318 (1986));

"RBS" is a ribosomal binding site;

"NdeI" is a restriction recognition site containing ATG translational start codon;

"MCS" represents multiple cloning sites;

"Gene X" represents the gene of interest cloned in the coding orientation relative to Perm E* promoter as shown by the arrow;

"Ter" is a terminator derived from transcription termination region of FKMT2 gene of Streptomyces MA6548 (ATCC No. 53770);

"hyg" is the gene encoding hygromycin phosphotransferase derived from *S. hygroscopicus* (Malpartida, F., et al., *Biochem. Biophys. Res. Commun.,* 117, 6–12 (1983));

"IE" is an integration element to direct insertion of the constructed vector into the chromosome of Streptomyces; and "ori" is the origin of DNA replication, required for propagation of the integrarive vector in *E. coli.*

Figure 3:
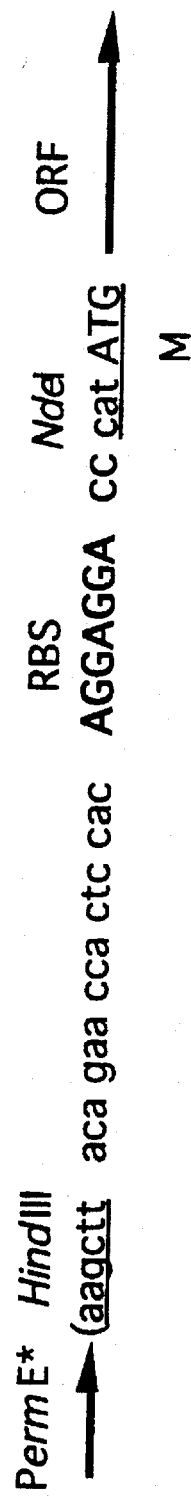
Figure 3B:

FIG. 3A and FIG. 3B: Depiction of two constructs in which the RBS was within two different sequence contexts (a(SEQ ID NO:12), b(SEQ ID NO:13)). The nucleotide sequence (SEQ ID NO:1) of the ribosome binding site (RBS) is

AGGAGGA and it is used in the construction of expression cassettes in two (a, b) sequence contexts (SEQ ID NO:12) and (SEQ ID NO:13), respectively.

Figure 4A:
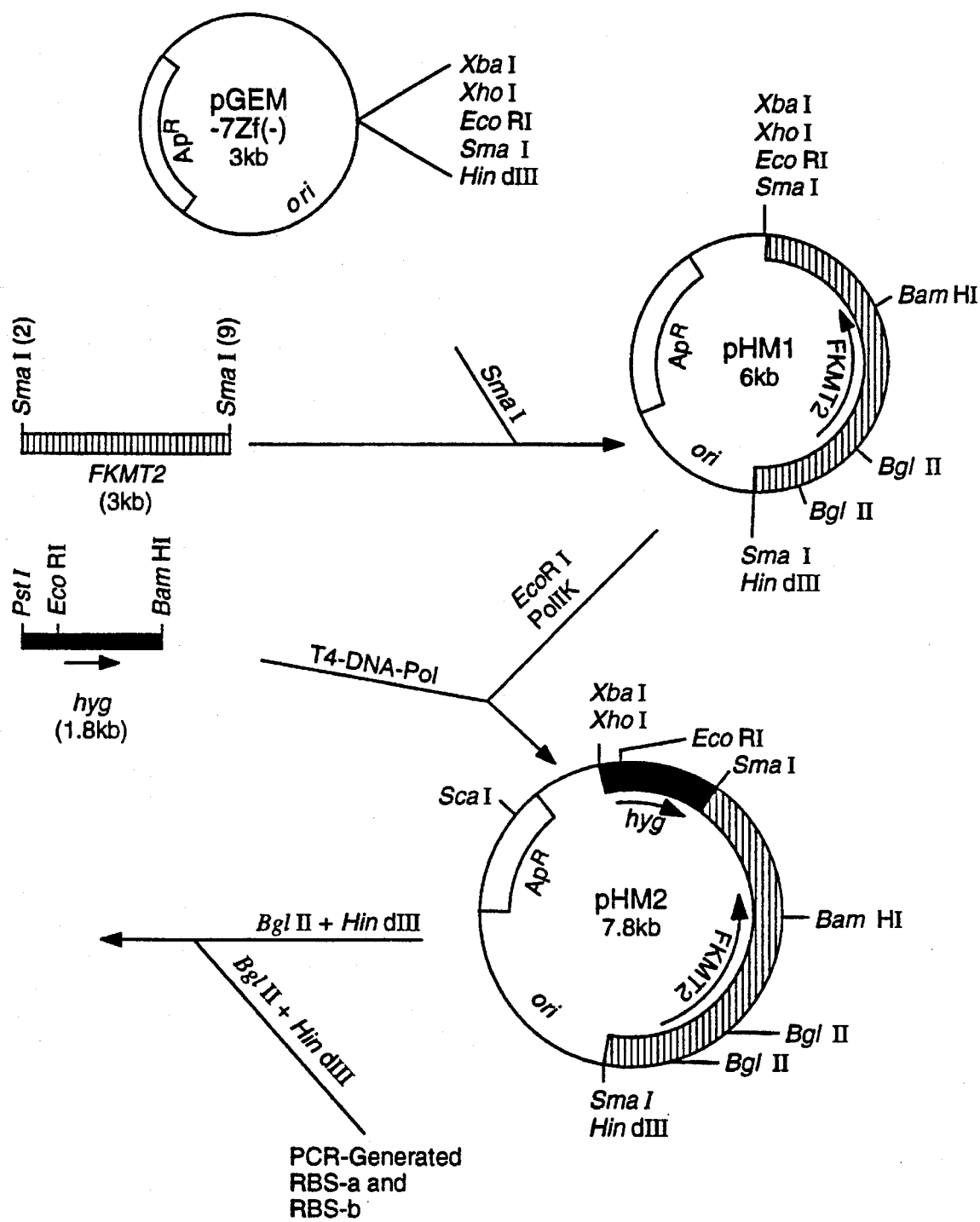
Figure 4B:
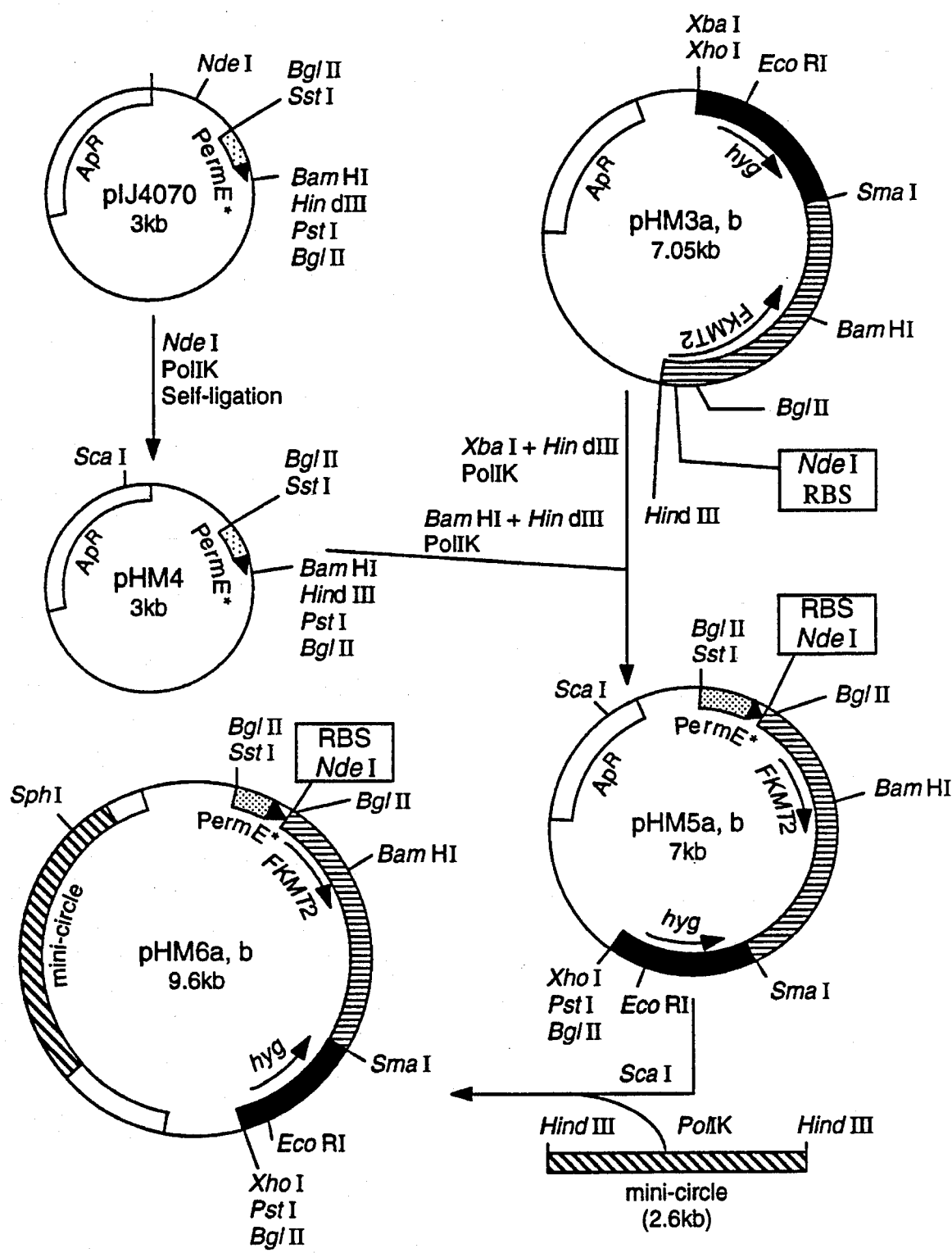

FIGS. 4a and 4b: Schematic representation of the construction of integrative expression vectors pHM6a and pHM6b that express the enzyme FKMT2.

Figure 5:
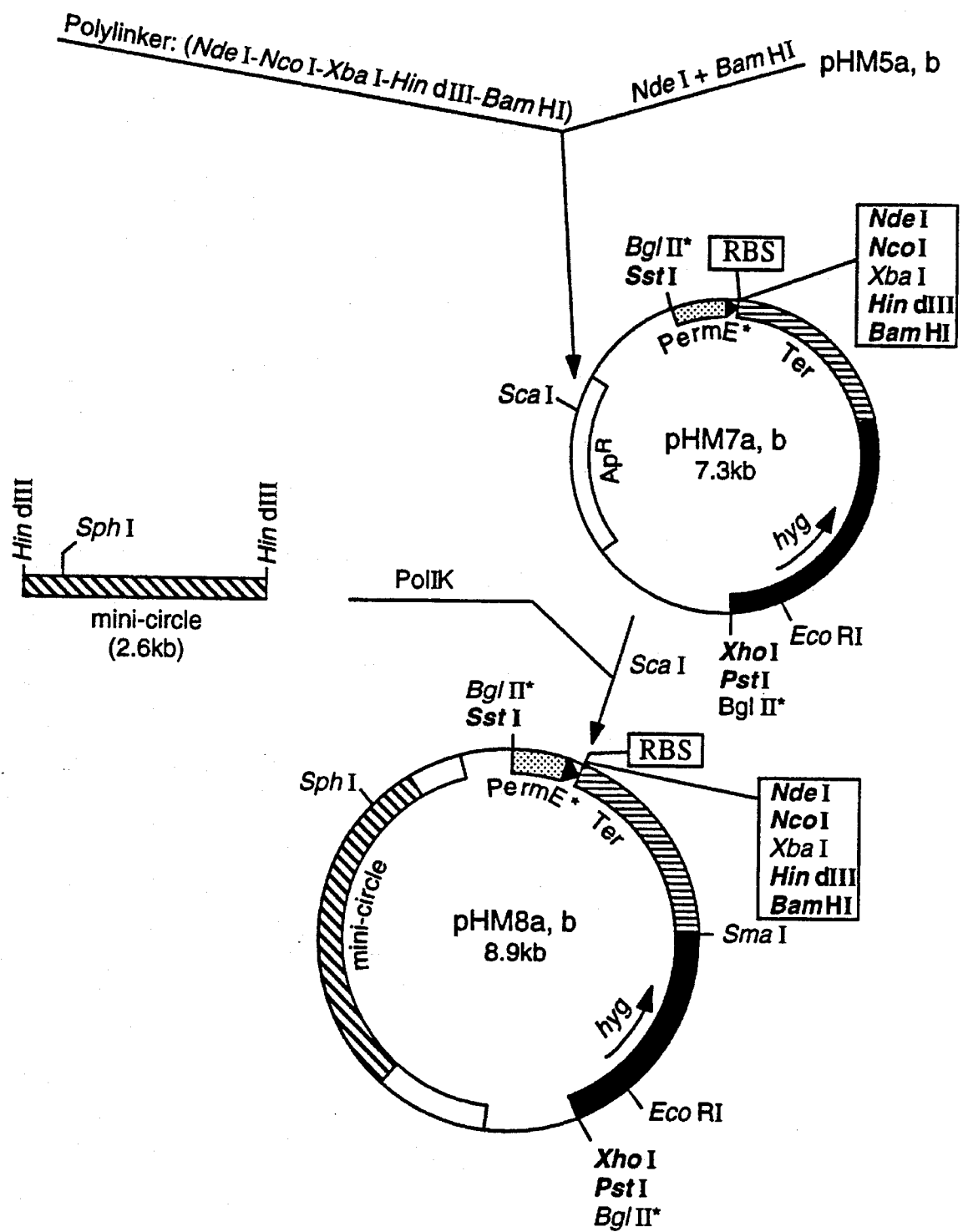

FIG. 5: Schematic representation of the construction of expression cassettes pHM7a and 7b and integrafive expression cassettes pHM8a and pHM8b. Unique restriction sites are shown in bold letters.

SUMMARY OF THE INVENTION

The present invention is directed to expression cassettes which are useful as vehicles for the transfer of single copy of desired genes through their integration into the chromosome of Streptomyces. Furthermore, the instant expression vectors are useful for the transfer of multiple copies of a gene of interest. via a low copy or high copy replicative plasmid, into any Streptomyces sp. More specifically, the present invention is directed to the construction of two *S. lividaris* recombinant strains, useful for the production of 31-desmethyl FK506-O-methyltransferase enzyme, which itself is useful for the conversion of 31-desmethyl-FK506 to FK506. In addition, the present invention is directed to a process for the specific methylation of 31-desmethyl-FK506 to FK506.

DETAILED DESCRIPTION OF THE INVENTION

The present invention is directed to integrarive expression constructs for heterologous and homologous expression of genes in a Streptomyces sp. These expression constructs are useful for the expression in Streptomyces of a desired protein of either prokaryotic or eukaryotic origin.

An integrative expression cassettes for the expression of a gene of interest in Streptomyces comprises:

(1) a strong promoter;

(2) a synthetic ribosome binding site;

(3) a translation start site embedded in NdeI recognition site;

(4) a multiple cloning site; and (5) a transcription terminator downstream from the cloning site:

in association with:

(i) an integration element to direct insertion of the construct into the Streptomyces genome;

(ii) a drug marker for selection both in E. coli and Streptomyces; and (iii) an E. coli replicon;

wherein the components (1)–(5) are associated in the specified order and each of the components (i), (ii), and (iii) may be independently associated either upstream or downstream of components (1)–(5).

The expression cassette more specifcally comprises the following elements:

(1) a strong constitutive promoter PermE*;

(2) a synthetic ribosome binding site derived from the RBS region of the gene encoding elongation factor Tu (tufl) of *Streptomyces ramocissimus*;

(3) an ATG start codon contained within the NdeI cloning site;

(4) a multiple cloning site, which gives additional cloning sites into which a gene of interest may be cloned;

(5) a transcription terminator derived from the terminator region of a methyltransferase gene involved in the biosynthesis of FK-506;

in association with:

(i) a hygromycin resistance gene which acts as selectable marker by inactivating the drug hygromycin B;

(ii) a minicircle as an integration element; and (iii) a Col El replicon;

wherein the components (1)–(5) are associated in the specified order and each of the components (i), (ii), and (iii) may be independently associated either upstream or downstream of components (1)–(5).

In an alternative embodiment of the present invention, the expression cassette more specifically comprises the following elements:

(1) a strong constitutive promoter PermE*;

(2) a synthetic ribosome binding site derived from a consensus *E. coli*-RBS sequence;

(3) an ATG start codon contained within the NdeI cloning site;

(4) a multiple cloning site, which gives additional cloning sites into which a gene of interest may be cloned;

(5) a transcription terminator derived from the terminator region of a methyltransferase gene involved in the biosynthesis of FK-506;

in association with:

(i) a hygromycin resistance gene which acts as selectable marker by inactivating the drug hygromycin B;

(ii) a minicircle as an integration element; and (iii) a Col El replicon;

wherein the components (1)–(5) are associated in the specified order and each of the components (i), (ii), and (iii) may be independently associated either upstream or downstream of components (1)–(5).

In the instant expression cassettes, the strong constitutive promoter PermE* is a promoter-up mutant (see Bibb, M. J., Janssen, G. R., "Unusual features of transcriptions and translation of antibiotic resistance genes in antibiotic producing Streptomyces", In *Fifth International Symposium on the Genetics of Industrial Microorganisms*, 309–318 (1986)) derived from the wild type promoter for erythromycin resistance gene of *Saccharopolyspora erythrea* (see Bibb, M. J., Ward, J. M., Cohen, S. N., "Nucleotide sequence encoding and promoting expression of 3 antibiotic resistance genes indigenous to Streptomyces", *Mol. Gen. Genetic* 199:26–36 (1985)).

The synthetic ribosome binding site is derived from the RBS region of the gene encoding elongation factor Tu (tufl) (a highly expressed gene in Streptomyces) (Vijgenboon, E., et al., *Microbiology*, 140, 983–998 (1994)) and/or a consensus *E. coli*-RBS sequence (Gold, L. and Stormo, G. D., *Methods in Enzymology*, 185, 89–93 (1990)) to ensure efficient translation.

The minicircle is a Streptomyces integration element derived from *Streptomyces coelicolor* and it functions to direct the insertion of the vector into the Streptomyces genome. This integration element is known to mediate integration of foreign genes in many Streptomyces that apparently have the attachment site for minicircle.

The Col El replicon is present for propagation in *E. coli*.

A specific embodiment of the present invention is directed to an expression vector for the overexpression of a gene of interest in Streptomyces comprising:

(1) a strong constitutive promoter, Perm E*, derived from erythromycin resistance gene of *Saccharopolyspora erythrea*;

(2) a synthetic ribosomal binding site (RBS) which include the heptamer (SEQ ID NO:2)

AGGAGGA in particular, wherein the synthetic ribosomal binding site (RBS) is present in the sequence context as depicted in sequence context (a) of FIG. 3, or in the sequence context as depicted in sequence context (b) of FIG. 3;

(3) a translation start site/cloning site which is a NdeI restriction site bearing a (SEQ ID NO:3)

CATATG recognition site and that serves both as cloning site and translation start site:

(4) a multiple cloning site; and (5) a terminator derived from the terminator region of the gene encoding FK506 methyltransferase, FKMT2 (isolated from MA6548) that is located downstream from the cloning site to prevent readthrough transcription;

in association with:

(i) a drug marker, which is hygromycin phosphotransferase and which is expressed both in *E. coli* and Streptomyces and confers hygromycin resistance to the host by inactivation of hygromycin B;

wherein the components (1)–(5) are associated in the specified order and the component (i) may be associated either upstream or downstream of components (1 )–(5).

The desired DNA may be recombinantly expressed by molecular cloning into an expression vector containing a suitable promoter and other appropriate transcription regulatory elements, as well as translational elements, and transferred into prokaryotic or eukaryotic host cells to produce recombinant protein. Techniques for such manipulations can be found described in Sambrook, J, Fritsch, E. F. and Maniatis, T. *Molecular Cloning, a Laboratory Manual,* Second edition, Cold Spring Habor Laboratory Press (1989) and are well known in the art.

"Expression cassettes" and "expression vectors" are defined herein as DNA sequences that are required for the transcription of cloned DNA and the translation of their mRNAs in an appropriate host. Such vectors can be used to express prokaryotic and eukaryotic DNA in a variety of hosts such as bacteria, bluegreen algae, plant cells, insect cells and animal cells.

Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

To employ the instant expression vectors the complete open reading frame of the gene of interest is cloned into the NdeI cloning site and the resulting plasmid is transformed into the target Streptomyces strain in which expression is to be studied. Integrants are selected by resistance to hygromycin. The presence of integrated vector and cloned gene may be verified by Southern analysis of the DNA prepared from hygromycin resistant strains. The resultant recombinant strains are very stable and addition of drug marker is not necessary to ensure maintenance of the construct during fermentation. Furthermore, the expression cassette along with the cloned gene may be placed on a low or high copy Streptomyces plasmid and transferred to any strain of interest for overexpression purposes required for biochemical and structural studies. A specific application of the vector is to express the gene encoding 31-O-methyltransferase, involved in methylation at position 31 of the immunosuppressive drug FK506, in *S. lividans*. The recombinant *S. lividans*, with integrated methyltransferase gene, successfully converted exogenously added 3 1-O-demethyl-FK506 to FK506, thus demonstrating functional expression of the cloned gene.

In a specific embodiment of the present invention, two integrative expression vectors pHM-6a and pHM-6b were designed and constructed. The two constructs in which the gene encoding 31-O-desmethylFK-506 O:methyltransferase (FKMT2), is under expression of a strong promoter, were incorporated into the genome of TK21 a strain of *Streptomyces lividans*. The resulting strains were then examined for the specific methylation of 31-O-desmethylFK-506 substrate which was added to the culture during fermentation. The purified fraction isolated from the culture was identified as FK-506 confiming expression of FKMT2 gene in a heterologous host. The developed strains thus prepared were fully capable of specific methylation of 31-O-desmethylFK-506.

Construction of the Integrative Expression Cassettes pHM6a and pHM6b Carrying the FKMT2 Gene The steps involved in the construction of integration expression vectors pHM6a and pHM6b, as schematically oulined in FIG. 4, are described below.

Figure 1:
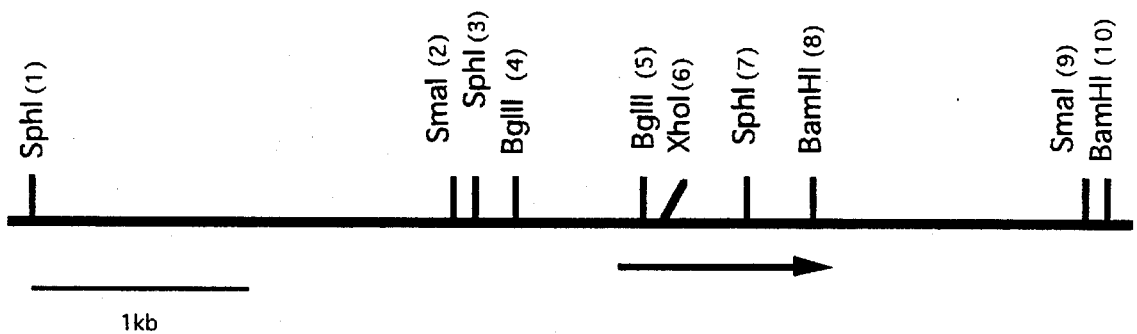
FIG. 1: Restriction map of FKMT2 coding region and surrounding area of Streptomyces sp. MA6548 (ATCC No. 53770), wherein the arrow indicates location, relative size and direction of transcription of FKMT2 gene.
Figure 2:
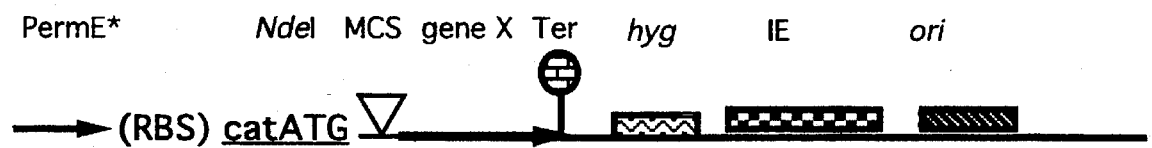

(1) A three kb SmaI fragment comprising the FKMT2 gene and flanking DNAs (sites 2 through 9 of FIG. 1) was cloned into the SmaI site of pGEM-7Zf(−) (Promega, Madison, Wis., U.S.A.) linearized with SmaI, resulting in plasmid pHM1.

(2) A 1.8 kb BamHI-PstI fragment containing hygromycin resistance gene (hyg) was isolated from plasmid pIJ963 (Hopwood, D. A., et al. *Genetic Manipulation of Streptomyces, A Laboratory Manual* (1985)) and after filling the ends with T4-DNA polymerase, was inserted into the polIK-filled EcoRI site of pHM1. This gave rise to plasmid pHM2 in which hyg gene was downstream from FKMT2 in the direction facing the methyltransferase (see pHM2 map in FIG. 4).

(3) Three oligodeoxynucleotide primers PC1, PC2, and PC3 were synthesized on Applied Biosystems (Foster City, Calif., U.S.A. ) DNA synthesizer model 380A. The three oligonucleotides were then used in two PCR reactions to make RBS-a and RBS-b as follows:

(3a) Preparation of RBS-a

PC1 sense primer was a 59 mer of the sequence (SEQ ID NO:4)

5'-GG AAG CTT ACA GAA CCA CTC CAC AGG AGG ACC CAT ATG AGC GCC GCG GTG GAG ACG TTG in which the underlined portion is derived from ribosome binding site region (−27 to −4) of *Streptomyces ramocissimus* elongation factor Tu (tufI). Immediately upstream and adjacent to RBS sequence a HindIII recognition site (SEG ID NO:5)

5'-AAGCTT depicted in bold letters and on the 3' end a NdeI recognition site (SEQ ID NO:3)

5'-CATATG depicted in bold letters were incorporated. The remaining nucleotide sequence of the primer corresponds to the nucleotide +4 to +24 at the N-terminal of FKMT2 coding region (depicted herein). The incorporation of NdeI at the translational start site changed the start codon of FKMT2 from GTG to ATG. The antisense primer PC2 was a 48 mer derived from the FKMT2 coding sequence corresponding to the complementary sequence to nucleotide 188 (5') to nucleotide 140 (3') (depicted herein) with the sequence (SEQ D NO:6)

ACG CTC GAG ATG AGC GAA GAG CGT GAA CAT GCC GAT GTT CGC GCC GAC

After amplification using PC1 and PC2 as primers and pHM1 as template DNA, the PCR products (220 bp) were purified and digested with HindIII and BglII and a 120 bp fragment was isolated and cloned between HindIII and BglII sites of pHM2 generating pHM3a.

(3b) Preparation of RBS-b

PC3 sense primer was a 62 mer of the sequence (SEQ ID NO:7)

5'-GGG AA GCT TAA GCT AAC GTA AGG AGG AAA AA CTA ATG AGCG CCG CGG TGG AGA CGT TGC GGC in which the underlined portion was according to a consensus RBS sequence characteristic of E. coli sequence (Gold, L. and Stormo, G. D., *Methods in Enzymology*, 185, 89–93 (1990)). Like RBS-a, RBS-b has HindIII recognition site on the 5' end and an NdeI site on the 3' end. The remaining nucleotides, 3' to NdeI, is derived from the FKMT2 coding region nucleotide +4 to +28 (depicted herein).

Primer PC3 was used with primer PC2 in a PCR reaction with pHM1 as template and a fragment of 120 bp was isolated from HindIII-BglII digestion of the resulting PCR product, which was then inserted between similar sites of priM2 producing pHM3b.

(4) Plasmid plJ4070 which carries ermE* promoter ("PermE*") (Bibb, M. J., et al., *Fifth Int'l Symp. Genetics Ind. Microorganisms*, 309–318 (1986)) was digested with NdeI and its 5'-overhangs were filled-in with polIK and recircularized to give pHM4 in which the NdeI site had been eliminated.

(5) The 4 kb XbaI-HindIII fragments of pHM3a and pHM3b were excised and the ends were filled with polIK and ligated between BamHI and HindIII sites of priM4 after the ends were made blunt with polIK. This generated plamids pHM5a and pHM5b in which the FKMT2 gene was placed under transcriptional/translational control of PermE* and RBS, respectively.

(6) Plasmids pHM5a and pHM5b were made integrative by inserting the 2.6 kb blunt-ended HindIII-cut mini-circle fragment (Lidiate, D. J., et al., *Mol. and Gen. Genet.*, 203, 79–88 (1986)) into ScaI site producing pHM6a and pHM6b.

Construction of Expression Cassettes pHM7a and PHM7b and Integrative Expression Vectors pHM8a and PHM8b Expression cassettes pHM7a and pHM7b (of FIG. 5) were constructed by inserting a synthetic polylinker NdeI-NcoI-XbaI-HindIII-BamHI between NdeI and BamHI sites of pHM5a and pHM5b (FIG. 5). This treatment introduced 3 additional unique sites into pHM7a and 7b, next to the NdeI recognition site. The synthetic polylinker was made as follow. Two complementary oligonuclcoetides PL1 (SEQ ID NO:8):

5'-TAT GCC ATG GCT CTA GAG AAG CTT G and PL2 (SEQ ID NO:9):

5'-GAT CCA AGC TTC TCT AGA GCC ATG GCA were designed, synthesized and annealed. The duplex oligo which had an NdeI site overhang on the 5' end and a BamHI site overhang on the 3' end was ligated between NdeI and BamHI sites of pHM5a and pHM5b which had been prepared as noted above.

Plasmids pHM5a and pHM5b (FIG. 5) were cleaved with BamHI and NdeI and the larger (6.3 kb) fragment was isolated. This treatment removed most of the coding region of the FKMT2 and left behind its terminator region (Ter) which is within a 1.3 kb BamHI -SmaI fragment. The FKMT2 terminator contains several inverted repeats (two of which are marked in the FKMT2 sequence by underlined and overlined arrows) with the potential of forming stem and loop structures characteristics of rho-independent transcription termination regions of prokaryotic genes.

The polylinker, containing restriction recognition sites for NdeI, NcoI, XbaI, HindIII and BamHI, was then ligated between NdeI and BamHI sites of the isolated fragments to generate pHM7a and pHM7b.

Expression vectors pHM7a and 7b are multicopy E. coli plasmids (pUC18 derivatives) that carry 4 kb Streptomyces expression cassettes (FIG. 5). The cassettes are comprised of PermE*, RBS, polylinker, terminator and hyg resistance gene functional both in E. coli and Streptomyces as selectable marker. Furthermore, as shown in FIG. 5, expression cassettes can be released as a 4 kb BglII fragment (marked by astricks) from pHM7a and pHM7b. Other usable sites are SstI on the 5' end and XhoI and PstI on the 3' end of the 4 kb expression cassette which can be utilized to liberate the expression cassette as well. The expression cassettes may be placed onto both low and high copy Streptomyces replicalive plasmids for the overexpression of the genes of interest or they may be integrated into the genome via an integration element for introduction of single copy gene into the genome. One such an element is *Streptomyces coelicolor* A3 (Bibb, M. J., et al., *Fifth Int'l Symp. Genetics of Ind. Microorganisms*, 309–318 (1986)) mini-circle which is a 2.6 kb transposable element (Lidiate, D. J., et al., *Mol. and Gen. Genet.*, 203, 79–88 (1986)) and carries an integration function which recognizes a specific site in the genome of several Streptomyces species (Lidiate, D. J., et al., *Genetics of Industrial Microorganisms*, 49–56 (1987)). The mini-circle sequence, when cloned into a vector, can direct integration of the entire construct into the chromosome through homologous recombination between chromosomal attachment (att) site and mini-circle att site resulting in the formation of a stable recombinant strain. The mini-circle has a wide host range ((Lidiate, D. J., et al., *Genetics of Industrial Microorganisms*, 49–56 (1987)) and several Streptomyces species such as *S. avermitilis*, *S. lividans*, *S. glaucescense*, *S. parvulus*, and many others referenced in Lidiate, D. J., et al., *Mol. and Gen. Genet.*, 203, 79–88 (1986) have the att site for this element.

Furthermore, in cases in which Streptomyces species do not contain mini-circle att sites, another integration element may be used. This can be achieved by choosing a non-essential gene as a platform for the integration of the construct into the genome which requires cloning of the designated gene in place of the mini-circle in vectors pHM7a and pHM7b, followed by integration into the chromosome through homologous recombination between the vector copy and the chromosomal copy of the target gene. Any gene encoding a secondary metabolite enzyme may be employed for this purpose.

Integrative expression vectors pHM8a and pHM8b (FIG. 5) were made by inserting a 2.6 kb polIK-treated HindIII-cut minicircle fragment (Lidiate, D. J., et al., *Genetics of Industrial Microorganisms*, 49–56 (1987)) into ScaI site of pHM7a and pHM7b, as depicted in FIG. 5.

Construction of Recombinant Strains *S. lividans*-pHM6a and *S. lividans*-pHM6b: Integration of pHM6a and pHM6b into the Chromosome of *S. lividans*

Protoplasts of *Streptomyces lividans* TK21 (ATCC No. 55251) (Hopwood, D. A., et al., *Genetic Manipulation of Streptomyces, A Laboratory Manual* (1985)) were prepared and transformed with pHM6a and pHM6b DNA in two separate reactions. After overnight incubation at 30° C., plates were overlayed with nutrient soft agar containing hygromycin B sufficient to give a final concentration of 200 µg/ml (Hopwood, D. A., et al. *Genetic Manipulation of Streptomyces, A Laboratory Manual* (1985)). Plates were incubated for 2–3 additional clays and hyg-resistant transformants were tested for functional expression of FKMT2 as follow.

In the general proceure for employing the present vectors, a two step cloning procedure is employed. In the first step the gene of interest is inserted into the polylinker 3' of the NdeI site. In the second step a small synthetic DNA encoding a small portion of the N-terminal region of the protein is prepared in which NdeI is incorporated at the translational start site. The size of the synthetic DNA depends on the presence of a sensible restriction site closest to the ATG site at the beginning of the gene. The synthetic fragment so prepared replaces the corresponding portion of the gene already cloned into the vector. Incorporation of NdeI site at the start site of translation permits expression of the proteins in their authentic nonfused form which ensures functionality of the expressed proteins. The constructed vector is inserted into Streptomyces species of choice via mini-circle or by other means described above.

Integrants may be selected by resistance to hygromycin. The presence of vector and cloned gene may then be verified by Southern analysis (Sambrook, J. Fritsch, E. F. and Maniatis, T. *Molecular Cloning, a Laboratory Manual,* Second edition, Cold Spring Habor Laboratory Press (1989)) may be performed on the genomic DNA prepared from integrants. Integrated vectors are very stable and addition of drug is not necessary to keep the construct intact during fermentation. The presence of antibiotic drugmarker in the fermentation broth often causes problems by affecting the level of expression of genes of interest. Furthermore, in cases where the drug does not have any effect on the expression, the cost of drug can be a factor. Consequently, the use of the present integrative vector eliminates the deleterious effects on production and cost due to the presence of antibiotic. Moreover the constructed cassette can be placed on a Streptomyces replicating plasmid and transformed into the desired host strain for overexpression studies.

Expression of 31-O-desmethylFK-506
O:methyltransferase (FKMT2)

Employing pHM6a and pHM6b the gene (FKMT2) encoding 31-desmethyl FK506 methyltransferase was used to examine the potential of these vectors in expression of a foreign gene in *Streptomyces lividans*. As a result, two strains of *S. lividans,* Sl/pHM6a and Sl/pHM6b were obtained which were capable of conversion of the 31-desmethyl FK506 to FK506 after addition of substrate to the culture broth during fermentation. HPLC, NMR and MASS analysis of the purified fraction from the culture extracts established the identity of the product as FK506 confirming funtionality of the expressed methyltransferase.

The nucleotide sequence of the FKMT2 coding sequence and the terminator region (1150 base pairs) are depicted below. The GTG translation start site at position +1 and the TAG translation stop codon at position 781 are depicted in bold letters. Two sets of inverted repeats at the 3'-end of the TAG codon are underlined and overlined by arrows, respectively. The nucleotide sequence of the FKMT2 sequence and the terminator region (SEQ ID NO:10) is

```
  1 CGATGAACGA GGGCCTCGGG CTTTTCAGCC CGGCCGAGCT GCGGGTCACC

51 TGGGGTGCCG T
                    +1                                                +39
                       GTGAGCGCC GCGGTGGAGA CGTTGCGGCT GCCGAACGGG

+89
101 ACGAAGGTCG CGCACATCAA CGCGGGCGAG GCGCAGTTCC TGTATCGGGA

+139
151 GATCTTCACC GAGCGCTGCT ATCTGCGCCA CGGCGTGGAA CTGCGCCCCG

+189
201 GTGACGTGGT GTTCGACGTC GGCGCGAACA TCGGCATGTT CACGCTCTTC

+239
251 GCTCATCTCG AGCGTCCCGG CGTGACCGTG CACGCGTTCG AGCCCGCGCC

+289
301 GGTGCCGTTC GCCGCGCTGC GGGCGAACGC GGCACAGTAC GGCATCTCGG

+339
351 GCCGGGTGGA CCAGTGCGCG GTCTCCGACG AGCCCGGCGT ACGCAAGATG

+389
401 ACGTTCTACC CCGACGCCAC GCTGATGTCC GGCTTCCATC CGGACGCCGC

+439
451 GGCCCGCAAG GAGCTGTTGC GCACACTAGG CCTCAACGGC GGATACACCG

+489
501 CCGAGGACGT CGACGGCATG CTCGCCCACC TGCCCGACTC GGGCGAGGAG

+539
551 ATCGAGACCG CCGTGGTCCG CCTCTCCGAC ATCATCGCCG AGCGCCGCAT

+589
601 CGCGACGATC GGCCTCCTGA AGGTCGACGT GGAAAGGAGT GAACGGCAGG

+639
651 TCCTCGCCGG CATCGAAGAA GCCGACTGGC CCCGCATCCG CCAGGTCGTC

+689
701 GCGGAGGTCC ACGACGTCGA GGGCGCGCTC GACGAGGTCG TCGCGCTGCT
```

```
751 GCGCGGCCAT GGCTTCACCG TCGTCGCCGA GCAGGATCCG CTGTTCGCCG
                                                        +783
801 GCACGGACAT CCACCAGGTC GCCGCACGGC GTGCGAGCCA CTGA
                                                    ----...........
                                                    GCCGCC
                                                    ----------.
    -------------->  <----------------------.
851 GGGGCGCGGC TACCCGCACC GGCGGTCGCG GTCCGCGGGC TCGCCGACGT
    --------------->              <----------------------------.

901 CGGCCAGTTC CTTCGGAAGC TGCTGGCGGC CCTTCACCGC CAGCTTTGCG

951 GAACACGTTC GTGAGGTGCT GTTCCACCGT GCTGGCCGTG ACGAACAGCT

1001 GCTCGGCGAT CTCCCTGTTC GTACGCCCGA CCGCGGCCAG CGCGGCCACC

1051 CGCCGCTCCG ACTCCGTCAG TGACGCGATC CGCTGCCCCA GCGTCGCGTC

1101 CCAGGCCCCG CCGATGTCCG AGGGCTCCGC GCCGAGCCGC CGCAGGAGCG
```

In particular, the nucleotide sequence of the FKMT2 coding sequence from position +1 and +783 is the following sequence (SEQ ID NO:11):

The entire coding sequence of FKMT2, the gene encoding 31-desmethyl FK506-O-methyltransferase from Streptomyces (MA6548, ATCC 53770), was cloned into NdeI site of

```
              +1                                         +39
              GTGAGCGCC GCGGTGGAGA CGTTGCGGCT GCCGAACGGG
                                                          +89
ACGAAGGTCG CGCACATCAA CGCGGGCGAG GCGCAGTTCC TGTATCGGGA
                                                          +139
GATCTTCACC GAGCGCTGCT ATCTGCGCCA CGGCGTGGAA CTGCGCCCCG
                                                          +189
GTGACGTGGT GTTCGACGTC GGCGCGAACA TCGGCATGTT CACGCTCTTC
                                                          +239
GCTCATCTCG AGCGTCCCGG CGTGACCGTG CACGCGTTCG AGCCCGCGCC
                                                          +289
GGTGCCGTTC GCCGCGCTGC GGGCGAACGC GGCACAGTAC GGCATCTCGG
                                                          +339
GCCGGGTGGA CCAGTGCGCG GTCTCCGACG AGCCCGGCGT ACGCAAGATG
                                                          +389
ACGTTCTACC CCGACGCCAC GCTGATGTCC GGCTTCCATC CGGACGCCGC
                                                          +439
GGCCCGCAAG GAGCTGTTGC GCACACTAGG CCTCAACGGC GGATACACCG
                                                          +489
CCGAGGACGT CGACGGCATG CTCGCCCAAC TGCCCGACTC GGGCGAGGAG
                                                          +539
ATCGAGACCG CCGTGGTCCG CCTCTCCGAC ATCATCGCCG AGCGCCGCAT
                                                          +589
CGCGACGATC GGCCTCCTGA AGGTCGACGT GGAAAGGAGT GAACGGCAGG
                                                          +639
TCCTCGCCGG CATCGAAGAA GCCGACTGGC CCCGCATCCG CCAGGTCGTC
                                                          +689
GCGGAGGTCC ACGACGTCGA GGGCGCGCTC GACGAGGTCG TCGCGCTGCT
                                                          +739
GCGCGGCCAT GGCTTCACCG TCGTCGCCGA GCAGGATCCG CTGTTCGCCG
                                                          +783
GCACGGACAT CCACCAGGTC GCCGCACGGC GTGCGAGCCA CTGA
``` integrative vector shown in FIG. 1A with the help of PCR. Two constructs were made (pHM6a and pHM6b in FIG. 4) in which RBS was within two different sequence contexts. Both vectors were then integrated into the genome of *Streptomyces lividans*, a heterologous host. Expression of the methyltransferase enzyme was montitored by the conversion of 31-desmethyl FK-506 to FK-506 after addition of substrate to the culture broth during fermentation. In both cases 100% conversion of 31-desmethyl FK-506 to FK-506 was observed. However pHM6b construct seemed to be sligthly slower in its bioconversion ability. HPLC, NMR and MASS analysis of the culture extracts prepared from the pHM6a and pHM6b constructs confirmed the product to be FK-506.

The following examples are given for the purpose of illustrating the present invention and shall not be construed as being limitations on the scope or spirit of the instant invention.

EXAMPLE 1

General Methodology

Strains

1. *E. coli* strain JM109
2. Streptornyces strain *S. lividans* TK21

*E. coli*

All the methods, media and buffers used to handle *E. coli* were accordrig to Sambrook et al. (Sambrook, J. Fritsch, E. F. and Maniatis, T., *Molecular Cloning, a Laboratory Manual*, Second edition, Cold Spring Habor Laboratory Press (1989)) unless otherwise indicated. *E. coli* strains containing plasmids were grown in LB broth in the presence of antibiotic marker carried on the plasmid. The level of drugs used was 100 μg/ml for ampicillin, and 50 μg/ml of hygromycin B both obtained from Sigma. Plasmid preparation was done on 50 ml cultures using QIAGEN® columns (QIAGEN Inc. 9259 Eton Ave. Chatsworth, Calif. 91311 ). Preparation of *E. coil* competent cells for transformation, DNA manipulation such as restriction digestion, filling end reactions, ligation, agarose gel electrophoresis and hybridization by Southern analysis were carried out using standard methods described by Sambrook et al.(Sambrook, J. Fritsch, E. F. and Maniatis, T., *Molecular Cloning, a Laboratory Manual*, Second edition, Cold Spring Habor Laboratory Press (1989). Sequencing was conducted on double stranded DNA template by dideoxy chain termination method using sequenase version 2.0 (United States Biochemicals) following the recommendations supplied therewith. DNA fragment isolation was carried out using QIAEX® gel extraction protocol (QIAGEN Inc.)

Streptomyces

All of the procedures, media and buffers used to handle Streptomyces were according to Hopwood et al. (Hopwood, D. A., et al., *Genetic Manipulation of Streptomyces, A Laboratory Manual* (1985)) or standard modifications thereof. Streptomyces strains were grown in R5 broth for 2-3 days.

For plasmid preparation, strains were grown in R5 in the presence of drug as follows: thiostrepton at 10 μg/ml; and hygromycin B at 200 μg/ml. For protoplast preparations, glycine was included in R5 at 0.5%. Methods used for chromosomal DNA preparation, plasmid DNA isolation, protoplast preparation and transformation are described below. Other DNA manipulations were carried out as described as referenced herein for *E. coli* (Sambrook, J. Fritsch, E. F. and Maniatis, T., *Molecular Cloning, a Laboratory Manual*, Second edition, Cold Spring Habor Laboratory Press (1989) and for Streptomyces (Hopwood, D. A., et al. *Genetic Manipulation of Streptomyces, A Laboratory Manual* (1985)).

EXAMPLE 2

Streptomyces Chromosonal DSNA Isolation

Streptomyces cultures (50 ml), grown in R5 broth (Hopwood et al., *Genetic Manipulation of Streptomyces, A Laboratory Manual* (1985)), was centrifuged for 10 min and the supematant was discarded. 20 ml of 10.3% sucrose was added, vortexed and then centrifuged for 10 min. The supematant was discarded. Then 20 ml of lysozyme buffer (10.3% sucrose, 25 mM Tris-HCl pH 8.0, 25 mM EDTA and 5 mg/ml lysozyme) was added. The mixture was vortexed and incubated at 37° C. for 45 min. Proteinase K was added to 50 μg/ml and incubated at 37° C. for 15 min. Then, 2 ml of 20% SDS was added, mixed well and heated at 65° C. for 10 min. After cooled to room temperature in ice, the sample was extracted with an equal volume of acid phenol:chloroform and centrifuged all 3,000 g for 20 min. The supernatant was transferred to a fresh tube with a 25 ml wide-tip pipet. The acid phenol:chloroform extraction was repeated one more time. A 1/10 volume of 3M NaOAc and 2 volumes of isopropanol were added, mixed and left at room temperature for 15 min. The mixture was centrifuged at 8,000 g for 10 min. The supernatant was discarded and the tube was dried with a kimwipe. 5 ml of TE (10 mM Tris-HCl pH 8.0/1 mM EDTA) was added to the pellet. After it was dissolved, RNAase A was added to 50 μg/ml and incubated at 37° C. for 30 min. The mixture was extracted with 5 ml of neutral phenol:chloroform and centrifuged at 12,000 g for 15 min. The supernatant was transfered to a fresh tube and same amount of chloroform was added. The mixture was vortexed and centrifuged at 8,000 g for 5 min. The supernatant was transferred to a new tube. A 1/10 volume of unbuffered 3M NaOAc and equal volume of isopropanol were added and mixed. After leaving at room temperature for 15 min, the mixture was centrifuged at 8,000 g for 10 min. The supernatant was discarded. The pellet was washed with 10 ml of 70% ethanol (but care was taken not to vortex) and centrifuged at 8,000 g for 10 min. The supernatant was discarded. The inside of tube was dried with kimwipes and then dried in vacuum. The pellet was dissolved in 3 ml of TE and was stored at 4° C.

EXAMPLE 3

Plasmid Preparation From Streptomyces

Streptomyces culture (50 ml) was centrifuged at 10,000 g for 15 min. The pellet was resuspended in 40 ml of 10.3% sucrose and centrifuged. The supernatant was discarded. Lysis buffer (20 ml) (10.3% sucrose, 25 mM Tris-HCl pH 8.0, 25 mM EDTA) containing 2 mg/ml lysozyme was added, vortexed and incubated at 37° C. in water bath shaker for 45 min. Alkaline SDS (12 ml) (0.2M NaOH/2% SDS) was added and mixed. The sample was incubated for 15 min at 70° C. for small plasmids (under 12 kb) and 30 min at 55° C. for larger ones (above 12kb) and then cooled to room temperature. Acid phenol:chloroform (equal volume) was added and vortexed for a few min. The mixture was centrifuged at 12,000 g for 15 min. The supernatant was transferred to a clean centrifuge tube. A 1/10 volume of 3M unbuffered NaOAc and equal volume of isopropanol were added, mixed and left at room temperature for 10 min. The mixture was centrifuged at 10,000 g for 15 min. The supernatant was poured off and the tube was wiped off with kimwipes. The pellet was dissolved in 10 ml of 30 mM Tris-HCl pH 8.0, 50 mM NaCl, 5 mM EDTA pH 8.0, then extracted with 5 ml of acid phenol:chloroform and spun at 12,000 g for 15 min. The top layer was transferred to a new tube, extracted with 5 ml of chloroform and centrifuged again. The supernatant was transferred to a new tube. RNAse A was added to 50 µg/ml and incubated at 37° C. for 30 min. The sample was extracted with phenol:chloroform and chloroform as before. After centrifugation, the top layer was transferred to a new tube and the plasmid was precipitated with NaOAc/isopropanol as before. The plasmid DNA pellet was dissolved in 9 ml TE, 1 ml of 4 mg/ml EtBr. Then 10.3 g CsCl was added and dissolved completely. The mixture was transferred to a quick-seal tube. The tube was sealed and centrifuged at 37,000 rpm in Beckman 70.1 Ti rotor for 60 hours. The plasmid band was collected. The EtBr was extracted from the sample with the isopropanol saturated with TE and NaCl. The sample was dialyzed in TE overnight at 4° C. A 1/10 volume of 3M NaOAc pH 5.2 and 2.2 volume of 100% ethanol was added to the sample, mixed and placed at −20° C. for at least 1 hour, followed by centrifugation at 10,000 g for 20 min. The pellet was washed once with 70% ethanol and then dried in vacuum. The plasmid DNA was resuspended in 100–500 µl of TE and stored at −20° C.

EXAMPLE 4

Protoplast Preparation

Streptomyces cultures (50 ml) grown in R5 in the presence of glycine (0.5%) were harvested for 10 min in tabletop centrifuge. The cells were washed with 10.3% sucrose and centrifuged for 10 min as above. The pellet was suspended in 10 ml "P" medium (Hopwood et al., *Genetic Manipulation of Streptomyces, A Laboratory Manual* (1985)) containing 1.5 mg/ml lysozyme (Sigma) and incubated in a 30° C. water bath shaker for 30–75 min. After 15 min incubation, and every 10 min thereafter, cell suspension was checked under microscope to determine completion of proplast formation. Protoplasts were then filtered through a spore filter tube and spun for 7 min, at 3,000 rpm. The supernatant was poured off and pellet was resuspended in 10 ml of "P" buffer followed by 7 min centrifugation as above. The pellet was then resuspended gently in 3–5 ml of "P" buffer and stored in small aliquats at 80° C.

EXAMPLE 5

Transformation

Plasmid DNA or ligation mixes (100–500 ng) was added to 50 µl of protoplasts. 500 µl transfonnatoin buffer (25% PEG 1000 in "P" buffer (Hopwood, D. A., et al., *Genetic Manipulation of Streptomyces, A Laboratory Manual* (1985))) was added to the protoplast/DNA mixture and mixed gently. The transformation mixture (100 µl) was then plated on R2YE plates and incubated at 30° C. overnight. Plates were then overlayed (3 ml) with soft nutrient agar (Hopwood et al., *Genetic Manipulation of Streptomyces, A Laboratory Manual* (1985)) in the presence of antibiotic marker carried on the plasmid and incubated for an additional 3–4 days.

EXAMPLE 6

Bioconversion of 31-O-desmethylFK-506 to FK-506

The gene (FKMT2) encoding 3 1-O-desmethylFK-506 O:methyltransferase was introduced into TK21, a strain of *Streptomyces lividaris,* as described above. The resulting transformant was isolated and was grown in the seed and bioconversion media. One hundred milligrams of 31-O-desmethylFK-506 was then dissolved in 50 µl DMSO and the solution was added to the 500 ml bioconversion culture at the time of the transfer of the seed culture. At different time intervals, an aliquot of the bioconversion culture was withdrawn and examined for the formation of FK-506. The methylation of the 31-O-desmethylFK-506 started at about 18th hour of the incubation and continued until 651h hour, when there was complete conversion of the substrate. The conversion of the 31-O-desmethylFK-506 into FK-506 was also measured using established HPLC procedures. The conversion was basically quantitative with no sign of side product formation. In order to confirm the nature of the bioconversion product, 500 ml bioconversion culture was harvested after 66 hours. The culture was mixed with an equal volume of methanol and centrifuged. The resulting supernatant was extracted with methylene chloride and the organic phase was recovered. This extract was concentrated to dryness under reduced pressure and the residue was suspended in 25 ml of 25% acetonitrile. The resulting solution was applied on a semi-preparative reverse-phase column and the column was developed with a gradient of acetonitrile in water. The desired product was eluted with 60–80% acetonitrile which was worked-up to yield 65 mg of the purified FK-506 (NMR and mass spectra obtained for the isolated product were identical to those of the standard, FK-506).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims which follow and that such claims be interpreted as broadly as is reasonable.

What is claimed is:

1. An isolated DNA molecule encoding the enzyme 31-O-desmethylFK-506 O:methyltransferase (FKMT2) and its terminator region comprising the nucleotide sequence (SEQ ID NO:10):

```
  1 CGATGAACGA GGGCCTCGGG CTTTTCAGCC

CGGCCGAGCT GCGGGTCACC
              +1
 51 TGGGGTGCCG TGTGAGCGCC GCGGTGGAGA
                                   +39
             CGTTGCGGCT GCCGAACGGG
101 ACGAAGGTCG CGCACATCAA CGCGGGCGAG
                                   +89
             GCGCAGTTCC TGTATCGGGA
151 GATCTTCACC GAGCGCTGCT ATCTGCGCCA
                                  +139
             CGGCGTGGAA CTGCGCCCCG
201 GTGACGTGGT GTTCGACGTC GGCGCGAACA
                                  +189
             TCGGCATGTT CACGCTCTTC
251 GCTCATCTCG AGCGTCCCGG CGTGACCGTG
                                  +239
             CACGCGTTCG AGCCCGCGCC
301 GGTGCCGTTC GCCGCGCTGC GGGCGAACGC
                                  +289
             GGCACAGTAC GGCATCTCGG
351 GCCGGGTGGA CCAGTGCGCG GTCTCCGACG
                                  +339
             AGCCCGGCGT ACGCAAGATG
401 ACGTTCTACC CCGACGCCAC GCTGATGTCC
                                  +389
             GGCTTCCATC CGGACGCCGC
451 GGCCCGCAAG GAGCTGTTGC GCACACTAGG
                                  +439
             CCTCAACGGC GGATACACCG
501 CCGAGGACGT CGACGGCATG CTCGCCCAAC
                                  +489
             TGCCCGACTC GGGCGAGGAG
551 ATCGAGACCG CCGTGGTCCG CCTCTCCGAC
                                  +539
             ATCATCGCCG AGCGCCGCAT
601 CGCGACGATC GGCCTCCTGA AGGTCGACGT
                                  +589
             GGAAAGGAGT GAACGGCAGG
651 TCCTCGCCGG CATCGAAGAA GCCGACTGGC
                                  +639
             CCCGCATCCG CCAGGTCGTC
701 GCGGAGGTCC ACGACGTCGA GGGCGCGCTC
                                  +689
             GACGAGGTCG TCGCGCTGCT
751 GCGCGGCCAT GGCTTCACCG TCGTCGCCGA
                                  +739
             GCAGGATCCG CTGTTCGCCG
801 GCACGGACAT CCACCAGGTC GCCGCACGGC
                                  +783
             GTGCGAGCCA CTGAGCCGCC
851 GGGGCGCGGC TACCCGCACC GGCGGTCGCG
             GTCCGCGGGC TCGCCGACGT
901 CGGCCAGTTC CTTCGGAAGC TGCTGGCGGC
             CCTTCACCGC CAGCTTTGCG
951 GAACACGTTC GTGAGGTGCT GTTCCACCGT
             GCTGGCCGTG ACGAACAGCT
1001 GCTCGGCGAT CTCCCTGTTC GTACGCCCGA
             CCGCGGCCAG CGCGGCCACC
1051 CGCCGCTCCG ACTCCGTCAG TGACGCGATC
             CGCTGCCCCA GCGTCGCGTC
1101 CCAGGCCCCG CCGATGTCCG AGGGCTCCGC
             GCCGAGCCGC CGCAGGAGCG.
```

2. An isolated DNA molecule encoding the enzyme 31-O-desmethylFK-506 O:methyltransferase (FKMT2) comprising the nucleotide sequence (SEQ ID NO:11):

```
                      +1                                                        +39
                    GTGAGCGCC  GCGGTGGAGA  CGTTGCGGCT  GCCGAACGGG

+89
         ACGAAGGTCG  CGCACATCAA  CGCGGGCGAG  GCGCAGTTCC  TGTATCGGGA

+139
         GATCTTCACC  GAGCGCTGCT  ATCTGCGCCA  CGGCGTGGAA  CTGCGCCCCG

+189
         GTGACGTGGT  GTTCGACGTC  GGCGCGAACA  TCGGCATGTT  CACGCTCTTC

+239
         GCTCATCTCG  AGCGTCCCGG  CGTGACCGTG  CACGCGTTCG  AGCCCGCGCC

+289
         GGTGCCGTTC  GCCGCGCTGC  GGGCGAACGC  GGCACAGTAC  GGCATCTCGG

+339
         GCCGGGTGGA  CCAGTGCGCG  GTCTCCGACG  AGCCCGGCGT  ACGCAAGATG

+389
         ACGTTCTACC  CCGACGCCAC  GCTGATGTCC  GGCTTCCATC  CGGACGCCGC

+439
         GGCCCGCAAG  GAGCTGTTGC  GCACACTAGG  CCTCAACGGC  GGATACACCG

+489
         CCGAGGACGT  CGACGGCATG  CTCGCCCAAC  TGCCCGACTC  GGGCGAGGAG

+539
         ATCGAGACCG  CCGTGGTCCG  CCTCTCCGAC  ATCATCGCCG  AGCGCCGCAT

+589
         CGCGACGATC  GGCCTCCTGA  AGGTCGACGT  GGAAAGGAGT  GAACGGCAGG

+639
         TCCTCGCCGG  CATCGAAGAA  GCCGACTGGC  CCCGCATCCG  CCAGGTCGTC

+689
         GCGGAGGTCC  ACGACGTCGA  GGGCGCGCTC  GACGAGGTCG  TCGCGCTGCT

+739
         GCGCGGCCAT  GGCTTCACCG  TCGTCGCCGA  GCAGGATCCG  CTGTTCGCCG

+783
         GCACGGACAT  CCACCAGGTC  GCCGCACGGC  GTGCGAGCCA  CTGA  .
```

3. An integrative expression cassette for the expression of a gene of interest in Streptomyces comprising:
 (1) a promoter functional in Streptomyces species;
 (2) a synthetic ribosomal binding site (RBS) which comprises the heptamer (SEQ ID NO:2) AGGAGGA;
 (3) an ATG start codon;
 (4) a multiple cloning site, which gives additional cloning sites into which a gene of interest may be cloned;
 (5) a trancription terminator derived from the terminator region of a methyltransferase gene involved in the biosynthesis of FK-506, wherein the transcription terminator comprises the nucleotide sequence depicted in base 845 to base 1150 of (SEQ ID NO:10);
in association with:
 (i) a hygromycin resistance gene which acts as selectable marker by inactivating the drug hygromycin B;
 (ii) a minicircle as an integratoin element, wherein the minicircle is a *Streptomyces* integration element derived from *Streptomyces coelicolor* and wherein the nucleotide sequence of the minicircle comprises the ATT sequence; and
 (iii) a Col El replicon;
wherein the components (1)–(5) are associated in the specified order and each of the components (i), (ii), and (iii) may be independently associated either upstream or downstream of components (1)–(5).

4. The integrative expression cassette of claim 3 wherein the minicircle is replaced by any non-essential gene and is used as an integration element.

5. An integrative expression cassette for the expression of a gene of interest in Streptomyces comprising:
 (1) a promoter functional in Streptomyces species;
 (2) a synthetic ribosome binding site derived from a consensus *E. coli*-RBS sequence, wherein the sequence is contained within the sequence (SEQ ID NO:7);
 (3) an ATG start codon;
 (4) a multiple cloning site, which gives additional cloning sites into which a gene of interest may be cloned;
 (5) a transcription terminator derived from the terminator region of a methyltransferase gene involved in the biosynthesis of FK-506, wherein the transcription terminator comprises the nucleotide sequence depicted in base 845 to base 1150 of (SEQ ID NO:10);
in association with:
 (i) a hygromycin resistance gene which acts as selectable marker by inactivating the drug hygromycin B;
 (ii) a minicircle as an integration element, wherein the minicircle is a Streptomyces integration element derived from *Streptomyces coelicolor* and wherein the nucleotide sequence of the minicircle comprises the ATT sequence; and
 (iii) a Col El replicon;
wherein the components (1)–(5) are associated in the specified order and each of the components (i), (ii), and (iii) may be independently associated either upstream or downstream of components (1)–(5).

6. The integrative expression cassette of claim 5 wherein the minicircle is replaced by any non-essential gene and is used as an integration element.

7. An expression cassette for the overexpression of a gene of interest in Streptomyces comprising: (1) a promoter functional in Streptomyces species;

(2) a synthetic ribosomal binding site (RBS) which comprises the heptamer (SEQ ID NO:2) AGGAGGA;

(3) a translation start site/cloning site which is a NdeI restriction site bearing a (SEQ ID NO:3) CATATG recognition site and that serves both as cloning site and translation start site;

(4) a multiple cloning site; and (5) a transcription terminator derived from the terminator region of the gene encoding FK506 methyltransferase, wherein the transcription terminator comprises the nucleotide sequence depicted in base 845 to base 1150 of (SEQ ID NO: 10), and wherein the transcription terminator is located downstream from the cloning site to prevent readthrough transcription;

in association with:

(i) a drug marker, which is hygromycin phosphotransferase and which is expressed both in *E. coli* and Streptomyces and confers hygromycin resistance to the host by inactivation of hygromycin B;

wherein the components (1)–(5) are associated in the specified order and the component (i) may be associated either upstream or downstream of components (1)–(5).

8. The expression cassette of claim 7 wherein the synthetic ribosomal binding site (RBS) is of the sequence as depicted in (SEQ ID NO: 12) of FIG. 3A.

9. The expression cassette of claim 7 wherein the synthetic ribosomal binding site (RBS) is of the sequence as depicted in (SEQ ID NO:13) of FIG. 3B.

10. A Streptomyces host cell containing the integrative expression cassette of claim 3.

11. A Streptomyces host cell containing the integrative expression cassette of claim 5.

12. A process for using the integrative expression cassette of claim 3 comprising cloning the integrative expression cassette of claim 3 into a Streptomyces chromosome.

13. A process for using the integrative expression cassette of claim 5 comprising cloning the integrative expression cassette of claim 4 into a Streptomyces chromosome.

14. The process of claim 12 wherein the cloning is used in the development of a strain of Streptomyces which is capable of catalyzing an organic reaction.

15. The process of claim 12 wherein the cloning is used in the production of a catalytic protein.

16. The process of claim 13 wherein the cloning is used in the development of a strain of Streptomyces which is capable of catalyzing an organic reaction.

17. The process of claim 13 wherein the cloning is used in the production of a catalytic protein.

18. A process for using the interactive expression cassette of claim 3 comprising cloning the interactive expression cassette of claim 3 into a Streptomyces replicative vector.

19. The process of claim 18 wherein the cloning is used in the development of a strain of Streptomyces which is capable of catalyzing an organic reaction.

20. The process of claim 18 wherein the cloning is used in the production of a catalytic protein.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

A G G A G G A            7

( 2 ) INFORMATION FOR SEQ ID NO:2:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

A G G A G G A            7

( 2 ) INFORMATION FOR SEQ ID NO:3:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

C A T A T G            6

( 2 ) INFORMATION FOR SEQ ID NO:4:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

GGAAGCTTAC AGAACCACTC CACAGGAGGA CCCATATGAG CGCCGCGGTG GAGACGTTG        59

( 2 ) INFORMATION FOR SEQ ID NO:5:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

AAGCTT        6

( 2 ) INFORMATION FOR SEQ ID NO:6:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:6:

ACGCTCGAGA TGAGCGAAGA GCGTGAACAT GCCGATGTTC GCGCCGAC        48

( 2 ) INFORMATION FOR SEQ ID NO:7:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

GGGAAGCTTA AGCTAACGTA AGGAGGAAAA ACTAATGAGC GCCGCGGTGG AGACGTTGCG        60
GC        62

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

TATGCCATGG CTCTAGAGAA GCTTG        25

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

```
GATCCAAGCT TCTCTAGAGC CATGGCA                                           27
```

( 2 ) INFORMATION FOR SEQ ID NO:10:

( i ) SEQUENCE CHARACTERISTICS:
        ( A ) LENGTH: 1150 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

```
CGATGAACGA GGGCCTCGGG CTTTTCAGCC CGGCCGAGCT GCGGGTCACC TGGGGTGCCG       60
TGTGAGCGCC GCGGTGGAGA CGTTGCGGCT GCCGAACGGG ACGAAGGTCG CGCACATCAA      120
CGCGGGCGAG GCGCAGTTCC TGTATCGGGA GATCTTCACC GAGCGCTGCT ATCTGCGCCA      180
CGGCGTGGAA CTGCGCCCCG GTGACGTGGT GTTCGACGTC GGCGCGAACA TCGGCATGTT      240
CACGCTCTTC GCTCATCTCG AGCGTCCCGG CGTGACCGTG CACGCGTTCG AGCCCGCGCC      300
GGTGCCGTTC GCCGCGCTGC GGGCGAACGC GGCACAGTAC GGCATCTCGG GCCGGGTGGA      360
CCAGTGCGCG GTCTCCGACG AGCCCGGCGT ACGCAAGATG ACGTTCTACC CCGACGCCAC      420
GCTGATGTCC GGCTTCCATC CGGACGCCGC GGCCCGCAAG GAGCTGTTGC GCACACTAGG      480
CCTCAACGGC GGATACACCG CCGAGGACGT CGACGGCATG CTCGCCCAAC TGCCCGACTC      540
GGGCGAGGAG ATCGAGACCG CCGTGGTCCG CCTCTCCGAC ATCATCGCCG AGCGCCGCAT      600
CGCGACGATC GGCCTCCTGA AGGTCGACGT GGAAAGGAGT GAACGGCAGG TCCTCGCCGG      660
CATCGAAGAA GCCGACTGGC CCCGCATCCG CCAGGTCGTC GCGGAGGTCC ACGACGTCGA      720
GGGCGCGCTC GACGAGGTCG TCGCGCTGCT GCGCGGCCAT GGCTTCACCG TCGTCGCCGA      780
GCAGGATCCG CTGTTCGCCG GCACGGACAT CCACCAGGTC GCCGCACGGC GTGCGAGCCA      840
CTGAGCCGCC GGGGCGCGGC TACCCGCACC GGCGGTCGCG GTCCGCGGGC TCGCCGACGT      900
CGGCCAGTTC CTTCGGAAGC TGCTGGCGGC CCTTCACCGC CAGCTTTGCG GAACACGTTC      960
GTGAGGTGCT GTTCCACCGT GCTGGCCGTG ACGAACAGCT GCTCGGCGAT CTCCCTGTTC     1020
GTACGCCCGA CCGCGGCCAG CGCGGCCACC CGCCGCTCCG ACTCCGTCAG TGACGCGATC     1080
CGCTGCCCCA GCGTCGCGTC CCAGGCCCCG CCGATGTCCG AGGGCTCCGC GCCGAGCCGC     1140
CGCAGGAGCG                                                           1150
```

( 2 ) INFORMATION FOR SEQ ID NO:11:

( i ) SEQUENCE CHARACTERISTICS:
    ( A ) LENGTH: 783 base pairs
    ( B ) TYPE: nucleic acid
    ( C ) STRANDEDNESS: single
    ( D ) TOPOLOGY: unknown ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

```
GTGAGCGCCG CGGTGGAGAC GTTGCGGCTG CCGAACGGGA CGAAGGTCGC GCACATCAAC    60
GCGGGCGAGG CGCAGTTCCT GTATCGGGAG ATCTTCACCG AGCGCTGCTA TCTGCGCCAC   120
GGCGTGGAAC TGCGCCCCGG TGACGTGGTG TTCGACGTCG GCGCGAACAT CGGCATGTTC   180
ACGCTCTTCG CTCATCTCGA GCGTCCCGGC GTGACCGTGC ACGCGTTCGA GCCCGCGCCG   240
GTGCCGTTCG CCGCGCTGCG GGCGAACGCG GCACAGTACG GCATCTCGGG CCGGGTGGAC   300
CAGTGCGCGG TCTCCGACGA GCCCGGCGTA CGCAAGATGA CGTTCTACCC CGACGCCACG   360
CTGATGTCCG GCTTCCATCC GGACGCCGCG GCCCGCAAGG AGCTGTTGCG CACACTAGGC   420
CTCAACGGCG GATACACCGC CGAGGACGTC GACGGCATGC TCGCCCAACT GCCCGACTCG   480
GGCGAGGAGA TCGAGACCGC CGTGGTCCGC CTCTCCGACA TCATCGCCGA GCGCCGCATC   540
GCGACGATCG GCCTCCTGAA GGTCGACGTG GAAAGGAGTG AACGGCAGGT CCTCGCCGGC   600
ATCGAAGAAG CCGACTGGCC CCGCATCCGC CAGGTCGTCG CGGAGGTCCA CGACGTCGAG   660
GGCGCGCTCG ACGAGGTCGT CGCGCTGCTG CGCGGCCATG GCTTCACCGT CGTCGCCGAG   720
CAGGATCCGC TGTTCGCCGG CACGGACATC CACCAGGTCG CCGCACGGCG TGCGAGCCAC   780
TGA                                                                783
```

( 2 ) INFORMATION FOR SEQ ID NO:12:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

```
AAGCTTACAG AACCACTCCA CAGGAGGACC CATATG                             36
```

( 2 ) INFORMATION FOR SEQ ID NO:13:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:13:

```
AAGCTTAAGC TAACGTAAGG AGGAAAAACA TATG                               34
```